United States Patent [19]

Knop et al.

[11] Patent Number: 4,510,129

[45] Date of Patent: Apr. 9, 1985

[54] IMMUNOSTIMULATING AGENT

[75] Inventors: Jürgen Knop, Caldern; Hans-Harald Sedlacek; Friedrich R. Seiler, both of Marburg, all of Fed. Rep. of Germany

[73] Assignee: Hoechst Aktiengesellschaft, Frankfurt, Fed. Rep. of Germany

[21] Appl. No.: 406,531

[22] Filed: Aug. 9, 1982

Related U.S. Application Data

[63] Continuation of Ser. No. 11,944, Feb. 13, 1979, abandoned, which is a continuation-in-part of Ser. No. 795,233, May 9, 1977, abandoned.

[30] Foreign Application Priority Data

May 11, 1976 [DE] Fed. Rep. of Germany ....... 2620649

[51] Int. Cl.$^3$ ............... A61K 39/42; A61K 39/40; A61K 39/12; A61K 39/02

[52] U.S. Cl. ..................... 424/86; 424/87; 424/89; 424/92

[58] Field of Search ............... 424/86, 87, 89, 92

[56] References Cited

PUBLICATIONS

Bagshawe et al., Nature, vol. 218, pp. 1254 & 1255, (1968).
Bystryn et al., Chemical Abstracts, 81: 48374(2) (1974).
Sethi et al., Chemical Abstracts, 78: 109216(m) (1973).
Simmons et al., Chemical Abstracts, 74: 62752(h) (1971).

Primary Examiner—Jerome D. Goldberg
Attorney, Agent, or Firm—Curtis, Morris & Safford

[57] ABSTRACT

The invention relates to an agent for stimulating the immunologic reactivity, comprising a mixture of an antigen and neuraminidase.

6 Claims, No Drawings

IMMUNOSTIMULATING AGENT

This application is a continuation of application Ser. No. 11,944 filed Feb. 13, 1979 and now abandoned, which in turn is a continuation of application Ser. No. 795,233 filed May 9, 1977, now abandoned.

The invention relates to an agent for the stimulation of the immunologic reactivity, in particular the antibody formation and the stimulation of the cellular reactivity which is inducible by antigens.

It is well known that the immunologic response of organisms which has been provoked by the application of antigens can be influenced by the addition of certain substances. In the case of a promoting influence of such supporting components of immunologically active substances, these are designated adjuvants. Adjuvants fall under very different classes of substances. Their action mechanism still forms the object of speculations. Their quality can thus be tested by comparative tests only, so that any prediction on the action as adjuvant of a substance not yet tested is possible with difficulty only.

In view of the great economic importance of immunizing agents in the prophylaxis and in the therapy of a series of diseases, the finding of the action as adjuvant of a substance is of great economic interest.

Now, we have found that, surprisingly, the enzyme neuraminidase (glycoprotein-N-acetylneuraminylhydrolase, classified under EC. 3.2.1.18) is a valuable immunostimulating agent, a so-called adjuvant.

It is known that the immunogenicity of glycoproteins can be increased significantly by removal of the N-acetylneuraminic acid with the aid of the enzyme neuraminidase. However, in these cases the increase of the immunogenicity is clearly explained by the action of the neuraminidase on the antigen which sets free new antigenic determinants by the enzymatic attack on the glycosid portion of the glycoprotein. After separation of the N-acetylneuraminic acid radicals, the desialoglycoprotein may be used for the immunization separately from the neuraminidase.

According to the invention, it has been found that neuraminidase as supporting component of antigens promotes their action in immuno-systems. Accordingly, the subject matter of the invention is in the first instance an agent for the stimulation of the immunologic reactivity, consisting of a mixture of antigen and neuraminidase.

Furthermore, the invention provides processes for the stimulation of the immunologic reactivity in a host and for the preparation of an antiserum by appropriate administration of this agent.

Neuraminidase is used in these agents suitably in a quantity of 0.01–150, preferably 0.5–50, in many cases also 5–50, units per immunizing dose.

The term neuraminidase encompasses a series of known enzymes which are capable of splitting off the neuraminic acid from neuraminic acid-containing glycoproteins. Their isolation and purification is known from literature. The neuraminidases utilizable as adjuvants in the sense of the invention are characterized by their activity to hydrolyze the α-ketoside linkage between neuraminic acid and a sugar partner. Preferably, those neuraminidases are used which hydrolyze the linkages 2→3, 2→4, 2→6 and 2→8. Thus, particularly effective is the neuraminidase obtained from Vibrio Cholerae which is known to be capable of hydrolyzing all four linkage types. A similar activity has the neuraminidase of Clostridium perfringens. However, viral neuraminidases are active in the sense of the invention, even if they do not have the broad specificity of the bacterial enzymes. In addition to the neuraminidases which can be isolated from microorganisms, there may also be used neuraminidases which are obtainable from the plasma or organisms of vertebrate animals.

It is suitable to use such neuraminidase preparations as adjuvants which have been prepared with all the care required in the production of pharmaceuticals.

The quantity of the adjuvant neuraminidase to be added per dose of an antigen is suitably expressed in units of the activity of the enzyme. A neuraminidase unit is defined as the quantity of the enzyme which is required to set free in 15 minutes at 37° C. 1 microgram of N-acetylneuraminic acid from human $\alpha_1$-glycoprotein (Orosomucoid) in 0.05 molar sodium acetate buffer having a pH-value of 5.5 with the addition of 9 mg/ml of sodium chloride and 1 mg/ml of calcium chloride (E. Mohr and G. Schramm, Z. Naturf. 15 b, page 568, 1960 and Schultz et al., 1958). In view of the possibility that neuraminidase may exert an antigen-modifying activity on antigens which contain neuraminic acid, in the tests carried out within the scope of the invention in most cases antigens which are free from neuraminic acid have been used. However, this cannot limit the scope of the invention to such compounds, the more so as neuraminidase has hitherto not been used together with neuraminic acid-containing antigens for immunization. In general, the glycoprotein antigens incubated with neuraminidase were washed several times after incubation and in this manner the neuraminidase was removed.

The removal (washing) of a quantity of neuraminidase first added to the antigen does not lead to a significant stimulation of the immuno-response to the antigen. A germ suspension of *Escherichia coli* germs which is free from neuraminic acid produces in mice, in the presence of neuraminidase, an earlier antibody reaction on the one hand, but, on the other hand, higher antibody levels in the serum that a germ suspension which is free from neuraminidase.

This was proved by the following test:

Mice were immunized intraperitoneally with $2 \times 10^8$ germs of killed E. coli/mouse together with various amounts of Vibrio Cholerae neuraminidase. For one part of the mice the neuraminidase was first added to the killed E. Coli germs, then the neuraminidase was removed from the germs by centrifugation of the germs, these were re-suspended in a suitable buffer medium and this measure was repeated three times. Another part of the mice received the E. Coli germs together with Vibrio cholera neuraminidase.

Table 1 shows the antibody titers in the blood of the various groups of mice on the 5th and 20th day after the immunization had been effected.

TABLE 1

| Immunization of mice with E. Coli germs which were free from neuraminic acid | | | |
|---|---|---|---|
| Antigen E. Coli + $2 \times 10^8$/ | Adjuvant Vibrio Cholerae Neuraminidase | Average antibody titer ± Standard deviation on the day | |
| | | 5 | 20 |
| yes | without | 10 ± 10 | 160 ± 120 |
| yes | 0,5 U | 60 ± 40 | 640 ± 240 |
| yes | 0,5 U washed | 10 ± 10 | 130 ± 60 |
| yes | 0,05 U | 10 ± 10 | 320 ± 140 |
| yes | 5 U | 160 ± 120 | 640 ± 320 |

TABLE 1-continued

Immunization of mice with *E. Coli* germs which were free from neuraminic acid

| Antigen *E. Coli* + $2 \times 10^8$/ | Adjuvant Vibrio Cholerae Neuraminidase | Average antibody titer ± Standard deviation on the day | |
|---|---|---|---|
| | | 5 | 20 |
| yes | 5 U washed | 10 ± 10 | 160 ± 100 |
| yes | 50 U | 80 ± 40 | 320 ± 160 |
| yes | 50 U washed | 10 ± 10 | 160 ± 80 |

The stimulation of the immunologic response becomes effective independently of the manner of administration of the antigen together with the neuraminidase, for example with intraperitoneal, subcutaneous, intradermal or intramuscular administration. The indicated antibodies were measured by the test for bactericidal activity.

Similar results were obtained in an immunization test with *Vibrio cholerae*. In the test for indirect hemagglutination with the aid of Vibrio cholerae lipopolysaccharide, results were obtained which were analogous to those given in Table 1.

The activity as adjuvant of neuraminidase can also be proved for virus antigens, for example the rubella virus (cf. Table 2).

TABLE 2

Immunization of mice with rubella virus

| Antigen Rubella virus | + | Adjuvant (Vibrio Cholerae Neuraminidase) | Mean hemagglutination- inhibition titer ± Standard deviation |
|---|---|---|---|
| yes | | 0,0 | 82 ± 98 |
| yes | | 0, 5 U per mouse | 105 ± 83 |
| yes | | 5 U per mouse | 461 ± 246 |
| yes | | 50 U per mouse | 89 ± 47 |
| no | | 5 U per mouse | 8 |

With the same system it is possible to demonstrate that a second immunization (booster immunization) can be carried out with very good success and that, here too, the virus suspensions combined with neuraminidase provoke an increased immunoresponse.

Instead of with a particular antigen material, as has been shown by way of example with a germ suspension of Escherichia Coli, Vibrio Cholerae and of rubella virus, the activity as adjuvant may also be proved with soluble antigens.

If, for example, an immiunization of mice is carried out with bovine serum albumine, an increase of the immunologic response is likewise found in the antigen preparations to which neuraminidase had been added. It can be proved with the aid of indirect hemagglutination of wether erythrocytes charged with bovine serum albumine.

In addition, neuraminidase is capable of breaking through an immunologic tolerance. For this purpose, quantities of neuraminidase per dose of about 0.5–5 units proved effective, whereas distinctly higher doses resulted in less distinct reactions.

With neuraminidase as adjuvant, an antibody response against sheep erythrocytes can furthermore be experimentally increased. This can be proved with the aid of the method, known as Jerne technique, of proving "plaque forming cells" in the spleens of the immunized animals. This test method also proves that a subsequent washing of the erythrocytes incubated with neuraminidase does not stimulate the immunologic response.

In addition to the previously demonstrated tests for increasing the antibody formation with the aid of the enzyme neuraminidase, the adjuvant of the present invention produces an improved resistance against infections.

Table 3 shows the results of a test in which mice have been immunized with S. typhimurium, with and without addition of an adjuvant. For this purpose, the mice were given on the 1st and 14th day of $4 \times 10^7$ each of killed germs of S. typhimurium. On the 28th day after the first injection, the mice were infected intravenously with $2 \times 10^5$ of virulent S. typhimurium. In order to determine the success of the immunization, some animals from the individual groups were sacrificed on the 1st, 3rd and 8th day after the infection, the liver and the spleen were removed and the live germs contained in them were determined. The following Table shows the number of live germs. The remaining animals of the individual groups were observed until the 28th day and the number of the surviving animals was determined. The percentual survival rate of the animals is likewise indicated in Table 3.

TABLE 3

| Antigen | Adjuvant | Live germs in liver and spleen on the day indicated ± standard deviation | | | Survival rate |
|---|---|---|---|---|---|
| | | 1 | 3 | 8 | |
| none | none | $8 \times 10^3 \pm 1 \times 10^3$ | $6 \times 10^4 \pm 2 \times 10^4$ | $4 \times 10^7 \pm 3 \times 10^7$ | 30% |
| S. typhi. | none | $8 \times 10^3 \pm 3 \times 10^3$ | $2,5 \times 10^5 \pm 2 \times 10^5$ | $6 \times 10^5 \pm 3 \times 10^5$ | 45% |
| S. typhi. | Neuraminidase 5 U per dose | $1,5 \times 10^4 \pm 0,2 \times 10^4$ | $2,5 \times 10^4 \pm 2,2 \times 10^4$ | $2,4 \times 10^4 \pm 2,3 \times 10^4$ | 70% |

The antigen S. typhimurium which contains neuraminidase lead to a distinctly reduced number of live germs in the organs and to an improved survival rate of the animals.

As has been shown by the test examples, neuraminidase is utilizable as adjuvant for the most various antigen preparations. Thus, it is a purpose of the invention to use neuraminidase with soluble as well as particular, live or dead antigens which can be isolated from microorganisms or from higher order animals. It is an essential feature of the invention that the neuraminidase is administered simultaneously with the antigen, against which a specifically increased immunologic response of the host treated should be obtained. The adjuvant has a particular practical importance, among others, in the increase of the resistance to infections, but also in the increase of the immunologic response upon administration of tissue cells, for example those of tumor tissue. Neuraminidase is used with particular advantage as adjuvant in the preparation of antisera against defined antigens, since in this case the same amount of the required antigen results in an important increase of the yield of the antibody to be isolated from the serum of the immunized animals.

We claim:

1. An agent for stimulating immunologic reactivity, consisting essentially of a physical admixture of an antigen wherein said antigen is Escherichia Coli, Vibrio Cholerae, rubella virus, wether erythrocytes or s.typhimurium and an effective amount of neuraminidase as adjuvant therefor containing 0.01 to 150 units of neuraminidase per dosage of antigen.

2. The agent as claimed in claim 1, containing 0.5 to 50 units of neuraminidase per dose of antigen.

3. Process for stimulating the immunologic reactivity in a warm-blooded animal, which comprises administering to said warm-blooded animal an effective amount of the agent as claimed in claim 1.

4. Process for stimulating the immunologic reactivity in a warm-blooded animal, which comprises administering to said warm-blooded animal an effective amount of the agent defined in claim 2.

5. A process for preparing an antiserum, which comprises administering an effecitve amount of the agent defined in claim 1 to an animal, withdrawing its blood after the formation of antibodies, and isolating the antiserum therefrom.

6. The process defined in claim 5 wherein the agent contains 0.01 to 150 units of neuraminidase per dose of antigen.

* * * * *